United States Patent [19]

Berger

[11] 4,141,980

[45] Feb. 27, 1979

[54] TRANQUILIZING TRANS-HEXAHYDRO-PYRIDO-INDOLE-2-ALKANOLS, -ALKANONES, -ALKANONITRILES, -ALKANOIC ACIDS, ESTERS AND AMIDES

[75] Inventor: Joel G. Berger, Summit, N.J.

[73] Assignee: Endo Laboratories Inc., Garden City, N.Y.

[21] Appl. No.: 860,212

[22] Filed: Dec. 13, 1977

Related U.S. Application Data

[63] Continuation-in-part of Ser. No. 675,112, Apr. 8, 1976, abandoned.

[51] Int. Cl.$^2$ .................. A61K 31/445; C07D 471/04

[52] U.S. Cl. ........................................ 424/256; 546/85; 546/87

[58] Field of Search ................ 260/293.55; 424/256

[56] References Cited

FOREIGN PATENT DOCUMENTS

2512109  10/1975  Fed. Rep. of Germany ...... 260/293.55
303833   12/1954  Switzerland .................... 260/293.55

*Primary Examiner*—Henry R. Jiles
*Assistant Examiner*—Richard A. Schwartz

[57] ABSTRACT

Certain 2-substituted trans-hexahydropyridoindoles are useful as major tranquilizers in warm-blooded animals or are useful as intermediates for producing such major tranquilizers.

52 Claims, No Drawings

TRANQUILIZING TRANS-HEXAHYDRO-PYRIDO-INDOLE-2-ALKANOLS, -ALKANONES, -ALKANONITRILES, -ALKANOIC ACIDS, ESTERS AND AMIDES

CROSS-REFERENCE TO RELATED APPLICATIONS

This application is a continuation-in-part of U.S. Ser. No. 675,112, filed Apr. 8, 1976, now abandoned.

BACKGROUND OF THE INVENTION

U.S. Pat. No. 3,991,199, issued Nov. 9, 1976 to Joel G. Berger, now U.S. Pat. No. 3,991,199, (which is a continuation-in-part of U.S. Patent Application Ser. No. 422,613, filed Dec. 6, 1973, now abandoned) discloses certain novel trans-2,3,4,4a,5,9b-hexahydro-1$\underline{H}$-pyrido[4,3-b]indoles of the general formula:

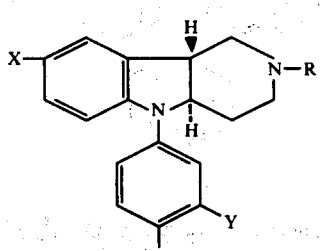

and their pharmaceutically suitable salts, where X, Y and R can be hydrogen or certain organic radicals, which indoles are useful as analgesics, sedatives, major tranquilizers, minor tranquilizers, muscle relaxants, and/or hypotensives.

In particular, Berger discloses the "nor" compound (the compound of Berger's formula I wherein R = H), which compound is a convenient starting material for virtually all of the compounds from within the scope of the present invention. In addition, Berger's parent application Ser. No. 422,613 disclosed the compound of formula I where X and Y = hydrogen and

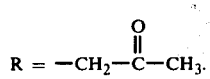

In addition, Heath-Brown, Chem. Ind. (London) pages 1595–6, 1969, discloses 2,3,4,4a,5,9b-hexahydro-2-methyl-5-phenyl-1$\underline{H}$-pyrido[4,3-b]indole hydrochloride. The hydrogen atoms attached to the 4a and 9b carbon atoms were in cis-relation to each other, because of the reduction method (Na/liq. NH$_3$) used. No utility for the compound is disclosed in this reference.

SUMMARY OF THE INVENTION

This invention relates to a class of novel compounds of the following formula:

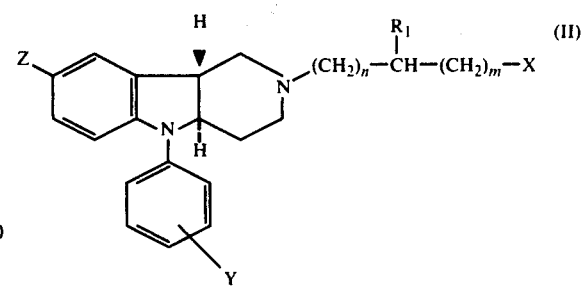

wherein
Z = H, F, Cl, or Br;
Y = H, F, Cl, Br, or OCH$_3$;

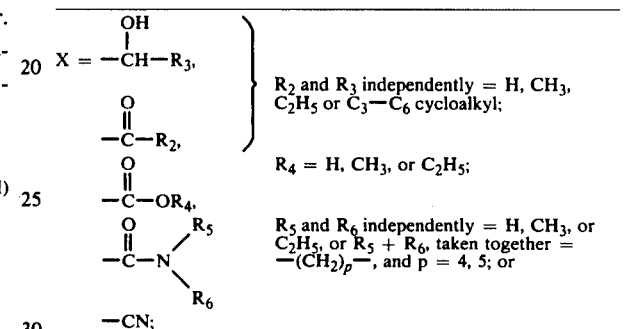

R$_1$ = H, CH$_3$, or C$_2$H$_5$; and
m and n, independently, = 0–4;
provided that when m + n = o, R$_1$ ≠ C$_2$H$_5$; and acid addition salts thereof with pharmaceutically suitable acids.

The compounds of formula II are useful as CNS depressants with major tranquilizer activity or as intermediates for producing such major tranquilizers. That is, for a given compound, even though one of the two or more antipodes may not be useful as a tranquilizer per se, it would be useful for making another antipode.

Presently preferred compounds from within this scope include those where:

(a) m + n ≤ 4;

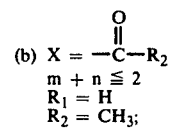
(b) m + n ≤ 2
R$_1$ = H
R$_2$ = CH$_3$;

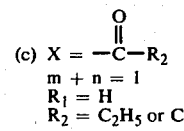
(c) m + n = 1
R$_1$ = H
R$_2$ = C$_2$H$_5$ or C$_3$–C$_6$ cycloalkyl;

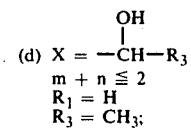
(d) m + n ≤ 2
R$_1$ = H
R$_3$ = CH$_3$;

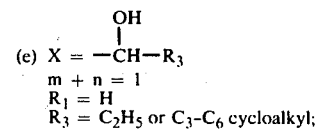
(e) m + n = 1
R$_1$ = H
R$_3$ = C$_2$H$_5$ or C$_3$–C$_6$ cycloalkyl;

-continued (f) $X = -\overset{\overset{\displaystyle OH}{|}}{CH}-R_3$
  $m + n \leq 4$
  $R_1 = H$
  $R_3 = H$;

(g) $X = -\overset{\overset{\displaystyle OH}{|}}{CH}-R_3$
  $m + n = 1$
  $R_1 = CH_3$
  $R_3 = H$;

(h) $X = -C\equiv N$
  $m + n \leq 4$
  $R_1 = H$;

(i) $X = -C\equiv N$
  $m + n = 1$
  $R_1 = CH_3$;

(j) $X = -\overset{\overset{\displaystyle O}{\|}}{C}-OR_4$
  $m + n \leq 4$
  $R_1 = H$
  $R_4 = H, CH_3$ or $C_2H_5$; and (k) $X = -\overset{\overset{\displaystyle O}{\|}}{C}-OR_4$
  $m + n = 1$
  $R_1 = CH_3$
  $R_4 = H, CH_3$ or $C_2H_5$.

Specifically preferred are the compounds:

a. (+)-trans-1,3,4,4a,5,9b-hexahydro-5-phenyl-2H-pyrido[4,3-b]indole-2-butyric acid, hydrochloride salt;

b. (±)-trans-1,3,4,4a,5,9b-hexahydro-5-phenyl-2H-pyrido[4,3-b]indole-2-butyric acid, hydrochloride salt;

c. (±)-trans-1,3,4,4a,5,9b-hexahydro-5-phenyl-2H-pyrido[4,3-b]indole-2-butyric acid, ethyl ester, hydrochloride salt;

d. (±)-trans-1,3,4,4a,5,9b-hexahydro-5-phenyl-2H-pyrido[4,3-b]indole-2-hexanoic acid, ethyl ester, hydrochloride salt.

The present invention also includes pharmaceutical compositions comprising a pharmaceutically suitable carrier and an effective amount of a compound of formula II, and a method for producing a tranquilizing effect in warm-blooded animals comprising administering an effective amount of a compound of formula II. The invention also includes processes for making the compounds of formula II as described hereafter.

DETAILED DESCRIPTION OF THE INVENTION

Synthesis of the Final Product Compounds

Each of the compounds of formula II can be made by one or more of the methods outlined below:

(1) The compounds of formula II wherein:

$n = 1$; and $m = 0$;

$X = -\overset{\overset{\displaystyle O}{\|}}{C}R_3, -\overset{\overset{\displaystyle O}{\|}}{C}-OR_4, -\overset{\overset{\displaystyle O}{\|}}{C}-N\overset{\displaystyle R_5}{\underset{\displaystyle R_6}{}}$ ; or $-C\equiv N$ ;

$R_4 = CH_3$ or $C_2H_5$; and $R_1, R_3, R_5, R_6, Z$ and $Y$ are as defined above; can be made as follows:

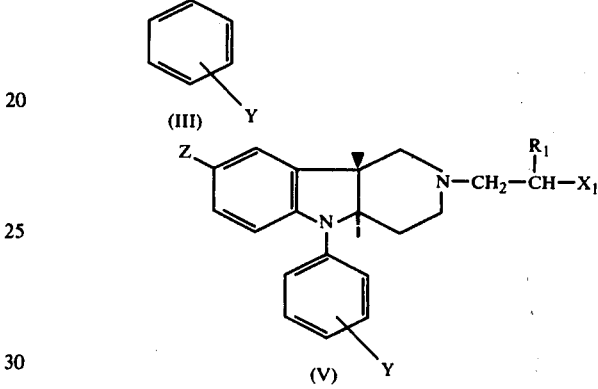

$X_1$ is those values of $X$ listed immediately above.

The reaction outlined immediately above can be conveniently carried out in a lower alkanol (such as methanol or ethanol), in an ether (such as diethyl ether, tetrahydrofuran or 1,4-dioxane), or in chloroform at temperatures of from 20°–101° C. for about 1–3 days.

(2) The compounds of formula II wherein:
$R_4 = CH_3$ or $C_2H_5$;
$m, n, R_1, R_2, R_3, R_5, R_6, X, Z, Y$ are as defined above; can be made as follows:

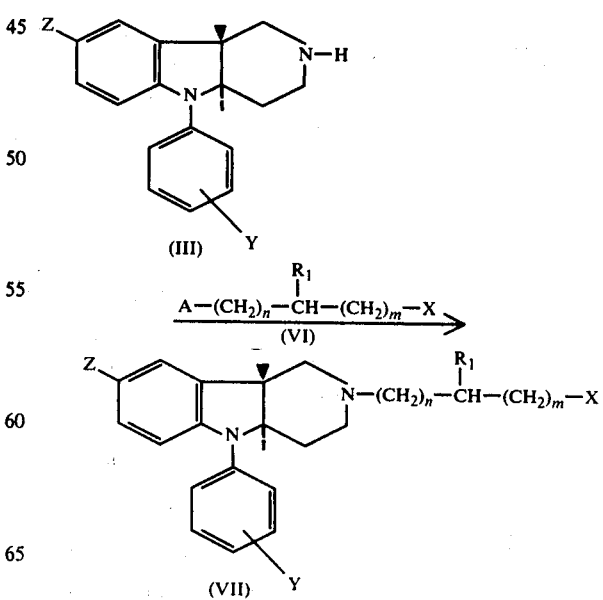

A is chlorine, bromine or iodine.

This reaction is most advantageously carried out in a highly polar, aprotic solvent (such as N,N-dimethylformamide (DMF), N,N-dimethylacetamide (DMAC) or hexamethylphosphoric triamide (HMPT) at temperatures of 60°–80° C. in the presence of an acid acceptor, such as triethylamine, powdered sodium carbonate, sodium bicarbonate, potassium carbonate or potassium bicarbonate.

When A is chlorine or bromine, the addition of potassium iodide to the reaction mixture will promote the reaction. When n is 1 and m = 0, and X is

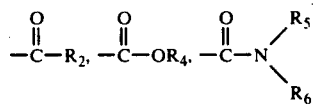

or —C≡N, method (I), above, is preferred.

(3) The compounds of formula II wherein:

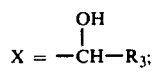

and m, n, $R_1$, $R_3$, Z, and Y are as defined above can be made as follows:

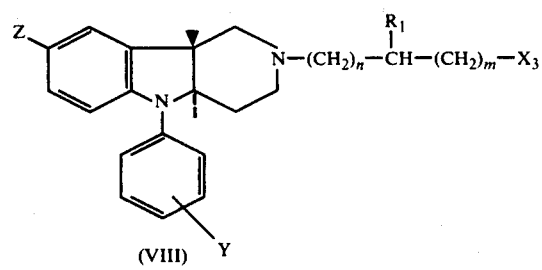

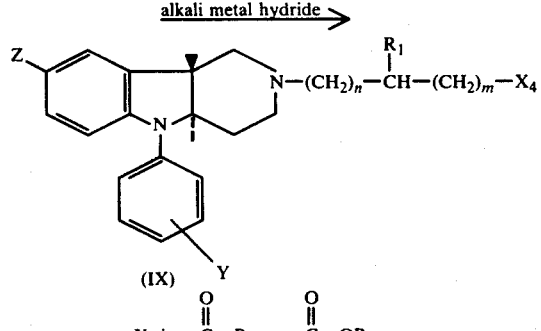

$X_3$ is $-\overset{O}{\underset{\|}{C}}-R_2$ or $-\overset{O}{\underset{\|}{C}}-OR_4$;

$R_4$ is $CH_3$ or $C_2H_5$;

$X_4$ is $-\overset{OH}{\underset{|}{CH}}-R_3$; and $R_2$ is as defined above.

The reduction shown above is carried out with an alkali metal complex hydride of boron or aluminum in a suitable solvent (such as $NaBH_4$ or $LiBH_4$ in a lower alkanol, such as methanol or ethanol, at 20°–30° C.; $LiAlH_4$ in diethyl ether or tetrahydrofuran (THF) at 35°–65° C.; or $NaAlH_2(OCH_2CH_2OCH_3)_2$ in benzene or toluene at 20°–110° C.).

(4) The compounds of formula II wherein m, n, $R_1$, Y and Z are as defined above; and

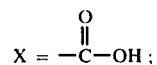

can be made as follows:

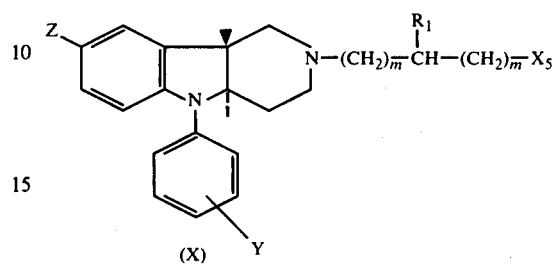

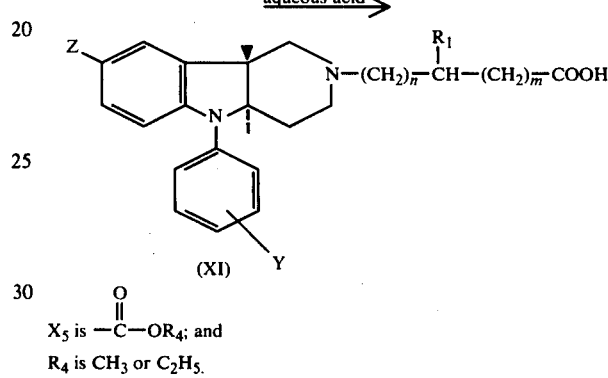

$X_5$ is $-\overset{O}{\underset{\|}{C}}-OR_4$; and $R_4$ is $CH_3$ or $C_2H_5$.

The hydrolysis shown above is carried out by refluxing for 15–60 minutes in an aqueous mineral acid (such as 6N HCl) leading to convenient isolation of the product as its mineral acid salt.

Synthesis of the Starting Material Compound

As indicated above, the starting material compound of formula III is the subject of copending U.S. Ser. No. 522,145. Its synthesis is described in detail therein and is summarized below:

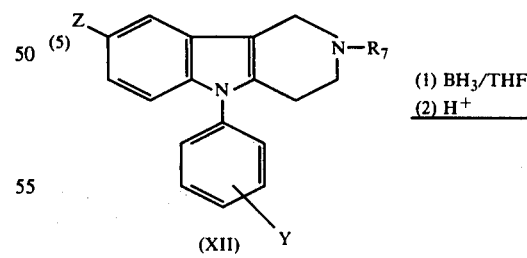

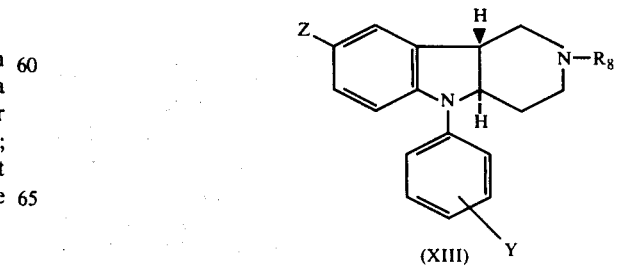

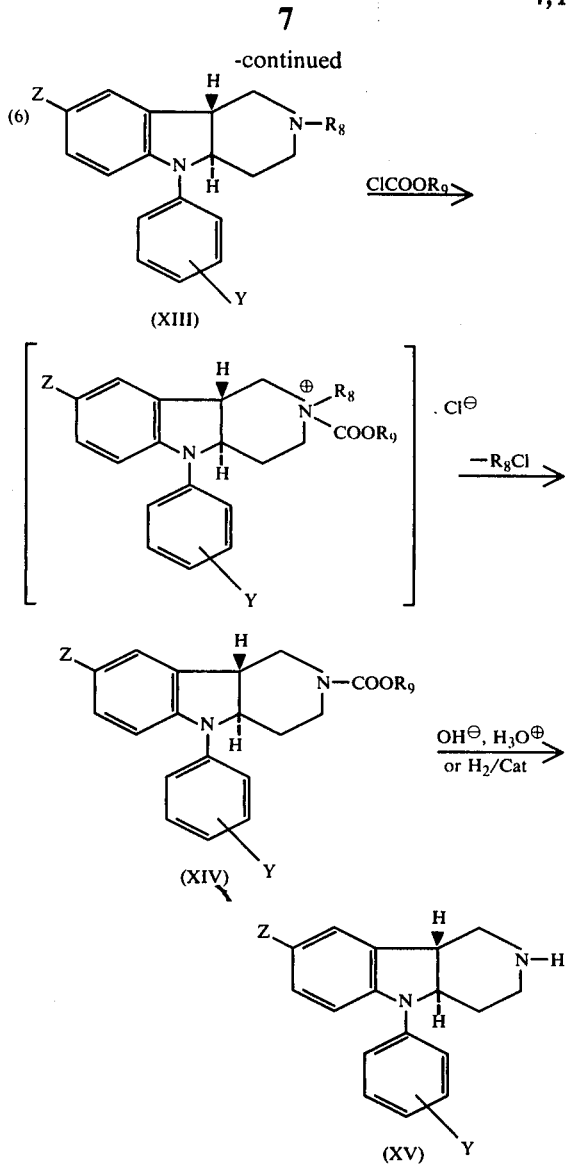

In the foregoing formulas, and whenever used herein: $R_7$ is the same as $R_8$ or is

where $R_{10}$ is phenyl, chlorophenyl, methylphenyl, methoxyphenyl, or cyclopropyl;

$R_8$ is methyl; ethyl; benzyl; benzyl ring-substituted with chloro, methyl or methoxy; or cyclopropylmethyl; and $R_9$ is $C_1$-$C_4$ alkyl; vinyl; benzyl; p-methylbenzyl; p-methoxybenzyl; or phenyl.

Reaction (5) starts with a 5-phenyl-2,3,4-5-tetrahydro-1H-pyrido[4,3-b]indole (formula XII). The formula XII starting materials are made by the Fischer Indole Synthesis, an acid catalyzed condensation between 4-piperidone or a 1-substituted-4-piperidone and a 1,1-diphenylhydrazine, according to the general procedure disclosed in Hörlein, U.S. Pat. No. 2,786,059 and Hörlein, Chem. Ber. 87, 463 (1954) followed (in the case of the unsubstituted 4-piperidone) by conventional alkylation or acylation.

The compound 1,1-diphenylhydrazine is commercially available. The necessary N-substituted 4-piperidones can be made simply by alkylation of 4-piperidone or acylation/reduction of the ethylene acetal of 4-piperidone followed by hydrolysis under conventional conditions.

Reaction (5), reduction of the tetrahydro precursors of formula XII to the hexahydro compounds of formula XIII, is usually carried out in tetrahydrofuran with a four-to-five-fold molar excess of boron hydride/tetrahydrofuran ($BH_3$/THF) complex at a temperature as low as 0° C. or as high as the reflux temperature of tetrahydrofuran. In some cases, a higher temperature is necessary or desirable; and the tetrahydrofuran solvent is diluted or replaced with a higher boiling ether such as diglyme or dioxane. The reaction temperature generally does not exceed 110° C. After the reduction, the mixture is acidified, for example, with about 4–10 molar hydrochloric acid, heated to about 100° C., allowed to cool, and neutralized with caustic.

The reduction of XII by treatment with $BH_3$/THF followed by treatment with acid produces compounds in which the hydrogens attached to the carbons in the 4a and 9b positions are in trans relationship. This has been confirmed by X-ray crystallography on the methiodide of (±)-2,3,4,4a5,9b-hexahydro-2-methyl-5-phenyl-1H-pyrido[4,3-b]indole.

Reaction Series (6)

The compound of formula XV cannot be produced directly by reduction with $BH_3$/THF followed by treatment with acid of the corresponding tetrahydro compound. Consequently, this compound must be produced from the compounds of formula XIII according to reaction series (6).

In series (6), the compound of formula XIII is first reacted with a chloroformate ClCOOR$_9$. This reaction can be carried out at a temperature in the range of 20° C. to 110° C., preferably 90° C. to 110° C., in an inert organic solvent such as benzene, toluene or dioxane. The quaternary ammonium salt initially produced upon reaction with the chloroformate is not isolated, and the reaction proceeds to the compound of formula XIV. The latter compound can, but need not, be isolated. Hydrolysis of the compound of formula XIV to produce the compound XV can be carried out in a $C_1$-$C_5$ alkanol containing 0–10% water and a hydroxide of potassium, sodium, lithium or calcium, at a temperature in the range of 65°–140° C. Alternatively, it can be carried out in aqueous mineral acid (e.g., acetic or hydrochloric acid) at a temperature in the range of 20°–110° C. The hydrogenolysis, applicable when $R_7$ is benzyl or substituted benzyl, can be carried out 1–3 atmopheres hydrogen pressure, a temperature in the range of 30°–60° C., and a platinum, palladium or Raney nickel catalyst.

Reaction Series (7)

When Z and/or Y ≠ H, compounds (XII) are more conveniently prepared according to the following scheme and as described in U.S. Pat. No. 4,001,263:

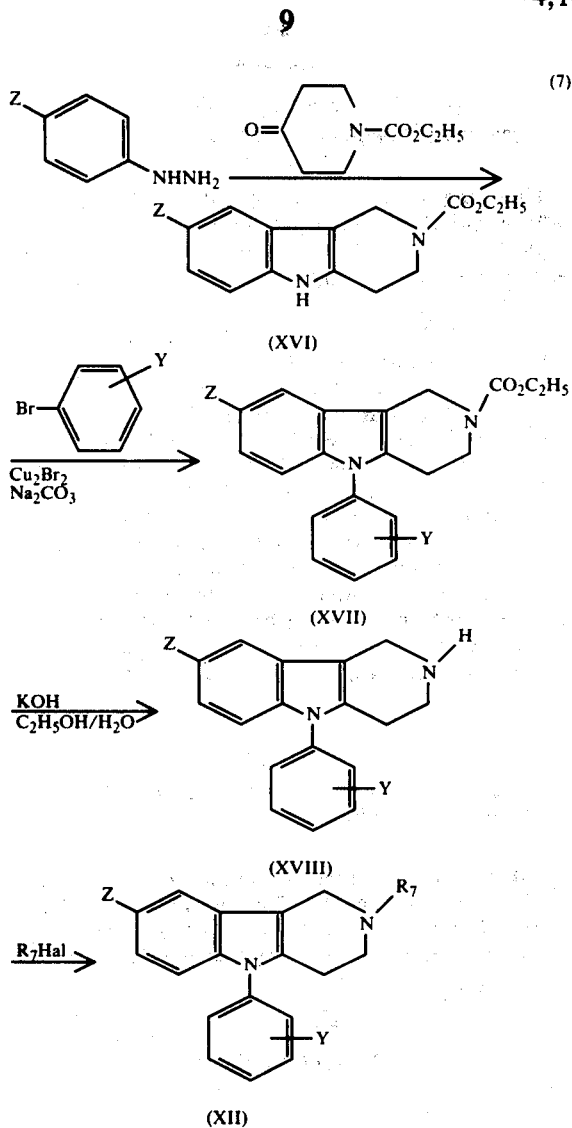

wherein Hal is a halogen or sulfonate ester, $R_7$, Z and Y are as defined above.

The compound of formula XV has two assymetric centers resulting from the reduction of the $\Delta^{4a,9b}$ to the trans-fused system. This compound can be separated into its dextro- and levo-rotatory enantiomers, which serve as starting materials for the optically active compounds of the present invention. Its separation is novel, and has been carried out as follows:

EXAMPLE 1

A hot solution of 95 grams (0.234 moles) of (+)-di-p-toluoyl-tartaric acid in 600 ml of ethanol was added to a hot solution of 58.5 grams (0.234 moles) of the compound XV racemate (Y and Z = H) in 600 ml of ethanol. A precipitate began to form almost immediately. The resulting mixture was allowed to cool slowly at ambient temperature for 2 hours whereupon the crystalline salt was filtered.

This material (40.7 grams) was suspended in ether and vigororously stirred with excess 10% sodium hydroxide solution. The solids dissolved and the ether layer was separated, washed with water, dried over potassium carbonate and filtered. The solvent was then evaporated in vacuo to give an oil which was then taken up in a small quantity of ethanol, cooled in ice, and scratched.

The resulting crystalline racemic compound separated and was filtered off. The filtrates were evaporated in vacuo to give an oil which was then dissolved in dry ether and treated with excess etheral HCl to give a white solid. This solid was filtered, washed with dry ether and air dried to give 21.1 grams of the dextro-rotatory salt $[\alpha]_D^{25}$ + 50.8° (c 1.4, $H_2O$).

Upon standing for several hours, the mother liquors of the (+)-di-p-toluoyl-tartrate salt deposited additional solids. This material was filtered (48.7 grams) and worked up exactly as described for the material above to give 17.9 grams of the levo-rotatory hydrochloride $[\alpha]_D^{25}$ − 49.6° (c 1.3, $H_2O$).

The following examples illustrate the preparation of the compounds of this invention.

EXAMPLE 2

(±)-trans-1,3,4,4a,5,9b-Hexahydro-5-phenyl-2H-pyrido[4,3-b]indole-2-propionic acid, ethyl ester hydrochloride Five grams (0.020 moles) of the compound of formula XV (Y and Z = H) was dissolved in 500 ml. of ethanol of was treated at room temperature with 3.3 ml. (0.030 moles) of ethyl acrylate. The reaction mixture was left standing at room temperature for 3 days and was then evaporated to dryness in vacuo. The residue was taken up in dry ether and the hydrochloride salt was made by treatment with excess dry hydrogen chloride. The precipatate was filtered and recrystallized from ethanol, m.p. 217° C. (dec.).

|        | % C   | % H  | % N  | % Cl |
|--------|-------|------|------|------|
| cal'd: | 68.28 | 7.05 | 7.24 | 9.16 |
| found: | 68.14 | 7.02 | 7.25 | 9.24 |

EXAMPLE 3

(±)-trans-1,3,4,4a,5,9b-Hexahydro-5-phenyl-2H-pyrido[4,3-b]indole-2-propionitrile Two grams (0.008 moles) of the compound of formula XV (Y and Z = H) was dissolved in 150 ml. of ethanol with slight warming. One ml. (0.015 moles) of acrylonitrile was then added at room temperature. The reaction mixture was left standing at room temperature for 5 days and was then evaporated to dryness in vacuo. The product was recrystallized from ethanol, m.p. 107.7°–108.5° C.

|        | % C   | % H  | % N   |
|--------|-------|------|-------|
| cal'd: | 79.17 | 6.98 | 13.85 |
| found: | 79.22 | 6.98 | 13.75 |

The following compounds can be made in a manner similar to that described in Examples 2 and 3 above:

TABLE 1

(structure shown: hexahydropyrido[4,3-b]indole with N-phenyl and N-(CH$_2$)$_n$-CH(R$_1$)-(CH$_2$)$_m$-X substituent)

(II) (n = 1) (m = 0)

| | X | R$_1$ | m.p. | (salt) |
|---|---|---|---|---|
| a. | —COOCH$_3$ | —H | | |
| b. | —COOCH$_3$ | —CH$_3$ | 204–205° C (dec.) | (HCl) |
| c. | —C≡N | —CH$_3$ | | |
| d. | —C(=O)—CH$_3$ | —H | 196° (dec.) | (HCl) |
| e. | —C(=O)—CH$_2$—CH$_3$ | —H | 96° | — |
| f. | —C(=O)-cyclopropyl | —H | | |
| g. | —C(=O)-cyclopentyl | —H | | |

EXAMPLE 4

(±)-trans-1,3,4,4a,5,9b-Hexahydro-5-phenyl-2H-pyrido[4,3-b]indole-2-butyric acid, ethyl ester hydrochloride Five grams (0.020 moles) of the compound of formula XV (Y and Z = H) was dissolved in 30 ml. of DMF, and 6.5 ml. (0.05 moles) of triethylamine, 5 grams (0.030 moles) of potassium iodide, and 4.5 grams (0.030 moles) of ethyl 4-chlorobutyrate were added. The reaction mixture was heated, and maintained at about 65° C. for about 30 hours with stirring. It was then cooled to room temperature, and the mixture was then poured into about 100 ml. of water and was then extracted 3 times with about 250 ml. of benzene. The organic phase was washed with water, dried with potassium carbonate and filtered. The aqueous phase was then extracted with about 100 ml. of chloroform. The organic phase was washed with water and dried with potassium carbonate. The chloroform filtrate was combined with the benzene filtrate and was evaporated in vacuo. The residue was taken up in about 50 ml. of ethanol, and 8 ml. of concentrated HCl was then added. The precipitate was then filtered and recrystallized from ethanol, m.p. 247° C. (dec.).

| | % C | % H | % N | % Cl |
|---|---|---|---|---|
| cal'd: | 68.89 | 7.30 | 6.99 | 8.44 |
| found: | 69.13 | 7.03 | 7.02 | 8.85 |

By using the appropriate functionalized halo compound and the compound of formula XV (Y and Z = H), the following compounds can be prepared in a manner similar to that described in Example 4 above:

TABLE 2

(structure shown: same hexahydropyrido[4,3-b]indole framework) (II)

| | R$_1$ | n | m | X | m.p. | salt |
|---|---|---|---|---|---|---|
| a. | H | 0 | 0 | —C(=O)—CH$_3$ | 219° (dec.) | (HCl) |
| b. | H | 2 | 0 | —C(=O)—CH$_3$ | 248–249.5° | (HCl) |
| c. | H | 4 | 0 | —C(=O)—CH$_3$ | | |
| d. | H | 1 | 0 | —C(=O)-cyclohexyl | 213.5–214.5° | (HCl) |
| e. | H | 2 | 0 | —C≡N | 256–258° | (HCl) |
| f. | H | 3 | 0 | —C≡N | | |
| g. | H | 4 | 0 | —C≡N | | |
| h. | H | 0 | 0 | —COOC$_2$H$_5$ | 199–199.5° | (HCl) |
| i | H | 2 | 0 | —COOC$_2$H$_5$ | 192–194° | (HCl); $[\alpha]_D^{25}$ = +41.9° (c 1.02, MeOH) |
| j. | H | 2 | 0 | —COOC$_2$H$_5$ | 188–191° | (HCl); $[\alpha]_D^{25}$ = −41.4° (c 0.95, MeOH) |
| k. | H | 3 | 0 | —COOC$_2$H$_5$ | 223–224° | (HCl) |
| l. | H | 4 | 0 | —COOC$_2$H$_5$ | 197–198° | (HCl) |
| m. | H | 9 | 0 | —COOC$_2$H$_5$ | 193.5–194.5° | (HCl) |
| n. | CH$_3$ | 0 | 1 | —COOC$_2$H$_5$ | 233–236° | (HCl) |

TABLE 2-continued

Structure (II):

(CH$_2$)$_n$—CH(R$_1$)—(CH$_2$)$_m$—X attached to 1,3,4,4a,5,9b-hexahydro-5-phenyl-2H-pyrido[4,3-b]indole N-2 position

| | R$_1$ | n | m | X | m.p. | salt |
|---|---|---|---|---|---|---|
| o. | H | 3 | 0 | —C(=O)—N(piperidine) | 161–166° | (HCl . H$_2$O) |
| p. | H | 2 | 0 | —C(=O)—N(piperidine) | 170–175° | (HCl) |
| q. | H | 2 | 0 | —C(=O)—N(C$_2$H$_5$)$_2$ | 198–203° | (HCl) |
| r. | H | 4 | 0 | —C(=O)—N(C$_2$H$_5$)$_2$ | 214.5–215° | (HCl) |
| s. | H | 4 | 0 | —C(=O)—N(piperidine) | 214–215° | (HCl) |
| t. | H | 1 | 0 | —C(=O)—N(piperidine) | 239–239.5° (dec.) | (HCl) |

EXAMPLE 5

(±)-trans-1,3,4,4a,5,9b-Hexahydro-5-phenyl-2H-pyrido[4,3-b]indole-2-butyric acid, hydrochloride 10.6 grams (0.264 moles) of (±)-trans-1,3,4,4a,5,9b-hexahydro-5-phenyl-2H-pyrido[4,3-b]indole-2-butyric acid, ethyl ester, hydrochloride (the compound of Example 4) was suspended in 80 ml. of 6N hydrochloric acid and was refluxed for 20 minutes. Immediately upon cooling, a precipitate was obtained which was filtered and washed with a small quantity of water giving the title compound, m.p. 238.5°–240° C. (dec.).

|  | % C | % H | % N | % Cl |
|---|---|---|---|---|
| cal'd: | 67.73 | 6.77 | 7.51 | 9.51 |
| found: | 66.75 | 6.71 | 7.70 | 9.85 |

Using an appropriate methyl or ethyl ester, the following acid-addition salts can be prepared in a manner similar to that described in Example 5.

TABLE 3

Structure: 1,3,4,4a,5,9b-hexahydro-5-phenyl-2H-pyrido[4,3-b]indole with N-2 substituent (CH$_2$)$_n$—CH(R$_1$)—(CH$_2$)$_m$—COOH

| | n | m | R$_1$ | m.p. | (salt) |
|---|---|---|---|---|---|
| a. | 0 | 0 | —H | 257–258° (dec.) | (HCl) |
| b. | 1 | 0 | —H | 150–153° (dec.) | (HCl) |
| c. | 1 | 0 | —CH$_3$ | 205–207° (dec.) | (HCl) |
| d. | 2 | 0 | —H | 273–274° (dec.) [α]$_D^{27}$ = +26.8° (c 1.00, H$_2$O) | (HCl) |
| e. | 2 | 0 | —H | 273–274° (dec.) [α]$_D^{27}$ = −25.5° (c 1.00, H$_2$O) | (HCl) |
| f. | 3 | 0 | —H | 233–234° | (HCl) |
| g. | 4 | 0 | —H | 279° (dec.) | (HCl) |
| h. | 9 | 0 | —H | 169–171° (dec.) | (HCl) |
| i. | 0 | 1 | —CH$_3$ | 158°–163° | (HCl) |

EXAMPLE 6

(±)-trans-1,3,4,4a,5,9b-Hexahydro-α-methyl-5-phenyl-2H-pyrido[4,3-b]indole-2-butanol, hydrochloride 8.1 grams (0.242 moles) of the ketone (±)-5-(trans-1,3,4,4a,5,9b-hexahydro-5-phenyl-2H-pyrido[4,3-b]indole-2-yl)-2-pentanone (compound b. from Table 2 above) was dissolved in 100 ml. of absolute ethanol, and 2.7 grams (0.726 moles) of sodium borohydride was added in one portion with stirring. The reaction mixture was stirred at room temperature overnight, and the resulting product was decomposed slowly by the addition of 2N hydrochloric acid. The reaction mixture was then made basic with 50% sodium hydroxide and the ethanol was separated from the aqueous layer. The ethanol was evaporated to near dryness and water was then added to the residue. This mixture was extracted with carbon tetrachloride, which was then dried with sodium sulfate, filtered and evaporated. The residue was taken up in 50 ml. of ethanol and 4 ml. of concentrated hydrochloric acid was then added. The precipitate was then filtered and washed with ethanol, yielding the title compound, m.p. 252.8°–253.8° C. (dec.).

|  | % C | % H | % H | % Cl |
|---|---|---|---|---|
| cal'd: | 70.84 | 7.85 | 7.51 | 9.50 |
| found: | 70.63 | 8.15 | 7.44 | 9.50 |

EXAMPLE 7

(±)-trans-1,3,4,4a,5,9b-Hexahydro-5-phenyl-2H-pyrido[4,3-b]indole-2-hexanol, hydrochloride 5.7 grams (0.015 moles) of (±)-trans-1,3,4,4a,5,9b-hexahydro-5-phenyl-2H-pyrido[4,3-b]indole-2-hexanoic acid, ethyl ester (compound 1. from Table 2 above), as the free base, was suspended in 50 ml. of dry THF and 570 mg. (0.015 moles) of lithium aluminum hydride in 50 ml. of THF was added under an atmosphere of nitrogen, resulting in an exothermic reaction. The resulting mixture was refluxed for 90 minutes, cooled and slowly decomposed with water. The inorganic salts were filtered off, washed with THF, and the combined THF was evaporated to an oily residue, which was taken up in chloroform and dried over sodium sulfate. After filtering off the sodium sulfate, the mother liquor was evaporated to an oil, which was taken up in ether and the ethereal solution was then filtered. On acidification with ethereal HCl, the solid which precipitated was digested in warm acetone, filtered, and recrystallized from ethanol. Filtration followed by washing yielded 1.7 grams of the title compound, m.p. 200°–202° C. (dec.).

Using the appropriate methyl or ethyl ester to prepare the corresponding primary alcohol, or using the appropriate ketone to prepare the corresponding secondary alcohol, the following alcohols can be prepared in a manner similar to that described in Examples 6 and 7.

TABLE 4

(structure II with $(CH_2)_n$—CH($R_1$)—CH(OH)—$R_3$ substituent)

| | n | $R_1$ | $R_3$ | m.p. | (salt) |
|---|---|---|---|---|---|
| a. | 0 | —H | —H | | |
| b. | 0 | —H | —CH$_3$ | | |
| c. | 1 | —H | —H | 283–287° | (HCl) |
| d. | 1 | —CH$_3$ | —H | 236–237° (dec.) | (HCl) |
| e. | 1 | —H | —CH$_3$ | | |
| f. | 1 | —H | —CH$_2$—CH$_3$ | 180–183° (with prior sintering) | (HCL) |
| g. | 1 | —H | cyclopropyl | | |
| h. | 1 | —H | cyclopentyl | | |
| i. | 1 | —H | cyclohexyl | 236–238° | — |
| j. | 2 | —H | —H | | |
| k. | 3 | —H | —H | | |
| l. | 4 | —H | —H | | |

Using the methods described in the examples above and in Reaction Series (7), the following compounds of formula II can be prepared:

TABLE 5

(structure with Z, Y substituents and $N—(CH_2)_n—CH(R_1)—(CH_2)_m—X$ side chain)

| Z | Y | n | m | $R_1$ | X |
|---|---|---|---|---|---|
| F | 4-F | 1 | 1 | —H | —COOH |
| F | 4-F | 1 | 1 | —H | —COOC$_2$H$_5$ |
| F | 4-F | 0 | 1 | —C$_2$H$_5$ | —COOH |
| Cl | 4-Cl | 2 | 0 | —H | —C≡N |
| Cl | 4-Cl | 3 | 0 | —H | —C(=O)—N(CH$_3$)$_2$ |
| Br | 4-Br | 1 | 1 | —H | —COOH |
| H | 3-OCH$_3$ | 1 | 1 | —CH$_3$ | —COOC$_2$H$_5$ |

Formulation and Use

As indicated above, the compounds of the present invention are active as CNS depressants and exhibit major tranquilizer activity which would be useful in the treatment of mental illnesses, including schizophrenia. Mental illnesses include psychoses and neuroses. The symptoms requiring treatment include anxiety, agitation, depression and hallucinations among others. The drugs used to treat psychoses include chlorpromazine and related phenothiazines, haloperidol and related butyrophenones, reserpine and related alkaloids, benzquinimide, tetrabenazine and other benzoquinolizines and chlorprothixene.

All of these drugs have side effects that limit their usefulness. The phenothiazines produce blood dyscrasias, jaundice, dermatological reactions, parkinsonism, dyskinesia and akathisia. They may also cause faintness, palpitation, nasal stuffiness, dry mouth, constipation and inhibition of ejaculations. Many of these same side effects are presented by the butyrophenones. Additional side effects are common with reserpine and similar compounds. These effects include mental depression, bradycardia, salivation, flushing, nausea and diarrhea.

There is a genuine need for psychotherapeutic agents which are effective and have fewer side effects than the drugs in use today. There is a need for such drugs which have different modes of action than the presently used drugs since none is completely effective.

The compounds of this invention can be administered in the treatment of psychiatric disorders, especially schizophrenia, according to the invention by any means that effects contact of the active ingredient compound with the site of action in the body of a warm-blooded animal. For example, administration can be parenterally, i.e., subcutaneously, intravenously, intramuscularly or intraperitoneally. Alternatively or concurrently, administration can be by the oral route.

The dosage administered will be dependent upon the age, health and weight of the recipient, the type and severity of disorder, the kind of concurrent treatment, if any, frequency of treatment and the nature of the effect desired. Generally a daily dosage of active ingredient compound will be from about 0.01 to 50 mg/kg of body weight. Ordinarily, from 0.02 to 20 and preferably 0.1 to 10 mg/kg per day in one or more applications per day is effective to obtain desired results. For more potent compounds of the present invention, for example, (±)-trans-1,3,4,4a,5,9,9b-hexahydro-5-phenyl-2H-pyrido[4,3-b]indole-2-butyric acid, hydrochloride, the daily dosage ranges are from about 0.01 to 10mg/kg, preferably 0.05 to 5 mg/kg and more preferably 0.1 to 2 mg/kg. For this compound, the tablet size would be about 10 mg to be given 1 to 4 times daily.

The CNS depressant activity of the compounds of the present invention was evidenced by tests conducted in female white mice in which exploratory activity loss, blepharoptosis, catalepsy, abdominal muscle tone loss and selectively greater loss of the lift reflux than that of the grip reflex were demonstrated. All of these properties are characteristic of major tranquilizers (see R. A. Turner, "Screening Methods in Pharmacology", Academic Press, New York, 1965).

Test Descriptions

Seventeen- to twenty-hour fasted female white mice, 16–20 grams each, were dosed orally with the test drug at 4, 12, 36, 108 and 324 mg/kg and were observed at 0.5, 2, 5 and 24 hours after drug administration for signs of exploratory activity loss (Explor.), blepharoptosis (Ptosis), catalepsy (Cat), abdominal muscle tone (M. tone), lift reflex (Lift) and grip reflex (Grip).

Exploratory Activity

The mouse is placed on a stainless steel wire mesh screen (8" × 12", 3 mesh per inch, ¼" mesh openings) "shoe-box" lid (1" high) and is observed for normal activities, such as nose movements, head movements with apparent visual examination of the area, and/or walking around on the screen. Normal mice respond within 2 to 3 seconds. Absence of or a marked depression of these activities for 5 seconds constitutes loss of exploratory activity.

Ptosis

The mouse is picked up by the tail and placed on the screen with its head facing the observer. Bilateral eyelid closure of 50% or more 2 seconds after placement is considered ptosis.

Catalepsy

The mouse is placed with its front paws on the edge of a stainless steel "shoe-box" cover, 1" high, covered with adhesive tape. Failure to remove both paws from the cover's edge within 5 seconds constitutes catalepsy.

Abdominal Muscle Tone

The observer gently strokes the abdominal musculature of the mouse with thumb and forefinger. Flaccidity (or rarely, tenseness) is recorded.

Grip and Lift Reflexes

The mouse is gently swung by the tail toward a horizontal 12-gauge wire tautly stretched 25 cm above the bench. After the mouse grasps the wire with its forepaws, its posterior end is held directly below the wire. A normal mouse grasps the wire with its forepaws and immediately lifts its hind limbs to the wire. Failure to grasp the wire with the forepaws in one of two trials constitutes loss of the grip reflex; failure to lift the hind limbs to grasp the wire with at least one hind paw within 5 seconds constitutes loss of the lift reflex.

Results

An $ED_{50}$, the calculated dose at which 50% of the mice would have responded, was calculated for each of the described parameters on each compound so tested. The $ED_{50}$'s are shown in Table 6 and may be compared to the data for a standard major tranquilizer, chlorpromazine.

TABLE 6

| Compound | Explor. | Ptosis | Cat. | M. Tone | Lift | Grip |
|---|---|---|---|---|---|---|
| Example 3 | 36.0 | 49.0 | 18.0 | 18.0 | — | — |
| Example 2 | 200.0 | 100.0 | 100.0 | 100.0 | 100.0 | >324.0 |
| Table 2, compound a. | 168.0 | 23.0 | 187.0 | 23.0 | 136.0 | 260.0 |
| Example 4 | 3.8 | 2.4 | 2.6 | 3.4 | 4.8 | >324.0 |
| Table 1, compound d. | 9.0 | 11.0 | 32.0 | 19.0 | 44.0 | 109.0 |
| Example 5 | 2.0 | 1.4 | 2.0 | 1.8 | 3.8 | 324.0 |
| Table 2, compound i. | 3.0 | 1.6 | 1.6 | 1.8 | 3.0 | 300.0 |
| Table 2, compound j. | 300.0 | 200.0 | 200.0 | >324.0 | >324.0 | >324.0 |
| Table 3, compound d. | 0.9 | 0.8 | 1.1 | 0.8 | 1.8 | 200.0 |
| Table 3, compound e. | 300.0 | >324.0 | 200.0 | 300.0 | >324.0 | >324.0 |
| Example 6 | <3.0 | <3.0 | 4.0 | <3.0 | 3.2 | 70.0 |
| Table 2, compound b. | <3.0 | <3.0 | 5.6 | 4.5 | 7.0 | 87.0 |
| chlorpromazine | 7.0 | 7.0 | 8.0 | 8.0 | 8.0 | 240.0 |
| Table 2, compound 1. | 5.0 | 3.2 | 7.0 | 9.7 | 9.7 | >324.0 |
| Table 3, compound g. | 4.4 | 2.6 | 9.7 | 5.6 | 7.8 | 300.0 |
| Example 7. | 1.1 | 1.9 | 2.6 | 1.7 | 4.4 | >324.0 |
| Table 2, compound h. | >324.0 | >324.0 | >324.0 | >324.0 | >324.0 | >324.0 |
| Table 1, compound b. | 20.0 | 36.0 | 60.0 | 60.0 | 60.0 | 300.0 |

TABLE 6-continued

| Compound | Explor. | Ptosis | Cat. | M. Tone | Lift | Grip |
|---|---|---|---|---|---|---|
| Table 2, compound d. | 4.5 | 6.0 | 6.0 | 3.6 | 19.0 | 290.0 |
| Table 4, compound i. | <4.0 | <4.0 | 7.0 | 7.0 | <4.0 | 60.0 |
| Table 3, compound c. | 7.0 | 12.0 | 7.0 | <4.0 | 20.0 | 200.0 |
| Table 2, compound m. | 4.5 | 4.0 | 15.0 | 10.0 | 12.0 | >324.0 |
| Table 3, compound h. | 5.6 | 9.0 | 12.0 | 7.0 | 21.0 | >324.0 |
| Table 4, compound d. | 5.6 | 8.0 | 36.0 | 23.0 | 40.0 | 400.0 |
|  | 7.8 | 18.7 | 13.6 | 29.0 | 23.2 | — |
| Table 1, compound e. | 7.0 | 20.0 | 7.0 | 12.0 | 60.0 | 200.0 |
| Table 4, compound f. | <4.0 | 7.0 | <4.0 | 7.0 | 12.0 | >324.0 |
| Table 2, compound f. | 23.2 | 23.2 | 36 | 26 | 40 | 109 |
| Table 2, compound g. | 5.6 | 5.0 | 5.6 | 5.0 | 12.0 | 109 |
| Table 2, compound i. | 4.0 | 2.1 | 7.0 | 3.6 | 6.2 | 62 |
| Table 2, compound o. | 2.9 | <3 | 15 | <3 | 3.6 | 19 |
| Table 4, compound b. | 40 | 15 | 187 | 136 | 187 | 450 |

The compounds can be formulated into compositions comprising a compound of formula II or a pharmaceutically suitable acid-addition salt thereof together with a pharmaceutically suitable carrier. The carrier can be either a solid or liquid and the compositions can be in the form of tablets, liquid-filled capsules, dry-filled capsules, aqueous solutions, non-aqueous solutions, suppositories, syrups, suspensions and the like. The compositions can contain suitable preservatives and coloring and flavoring agents. Some examples of the carriers which can be used in the preparation of the products of this invention are gelatin capsules; sugars, such as lactose and sucrose; starches; dextrans; cellulosics, such as methyl cellulose, cellulose acetate phthalate; gelatin; talc; steric acid salts; vegetable oils, such as peanut oil, cottonseed oil, sesame oil, olive oil, corn oil, and oil of theobroma; liquid petrolateum; polyethylene glycol; glycerin; sorbitol; propylene glycol; ethanol; agar; water; and isotonic saline.

In formulating the compounds, conventional practices and precautions are used. The composition intended for parenteral administration must be sterile either by using sterile ingredients and carrying out the production under aseptic conditions or by sterilizing the final composition by one of the usual procedures such as autoclaving under appropriate temperature and pressure conditions. Customary care should be exercised so that no incompatible conditions exist between the active components and the diluent preservative or flavoring agent, or in the conditions employed in preparation of the compositions.

Typical formulations of the type listed above, which may be used for the administration of these compounds are:

EXAMPLE 8

An appropriate size batch of tablets can be prepared so that each tablet will contain:

| Table 3, compound d. | 10 mg. |
|---|---|
| Colloidal Silicon Dioxide | 1 mg. |
| Starch | 20 mg. |
| Microcrystalline Cellulose | 70 mg. |
| Magnesium Stearate | 4 mg. |
| Plasdone | 7 mg. |

Mix the active ingredient with the Microcrystalline Cellulose and granulate with a PVP solution. Dry the above granulation and comminute through a proper size screen. Mix the Colloidal Silicon Dioxide, Starch, and the granulation. Add the Magnesium Stearate to the above mix by screening through a No. 30 mesh screen and mix for five minutes. Compress into proper size tablets.

EXAMPLE 9

Hard gelatin capsules can be prepared by filling standard two-piece hard gelatin capsules with the following mixture using conventional encapsulating equipment:

| Compound of Example 5 | 10 mg. |
|---|---|
| Lactose | 150 mg. |
| Talc | 12 mg. |
| Magnesium Stearate | 5 mg. |

EXAMPLE 10

A proper batch size of soft gelatin capsules can be prepared by injecting a mixture of active drug in soy bean oil into gelatin be means of a positive displacement pump. Each soft gelatin capsule will contain 10 mg. of active ingredient. The capsules are then washed in petroleum ether and dried.

EXAMPLE 11

An aqueous suspension for oral administration is prepared using conventional procedures so that each 5 ml. contains:

| Table 2, compound h. | 10 mg. | |
|---|---|---|
| Syrup | 40 % | v/v |
| Glycerin | 10 % | v/v |
| Sorbitol | 5 % | v/v |
| Sodium Benzoate | 5 mg. | |
| Methyl Cellulose | 5 % | w/v |
| Carboxy methyl cellulose | 5 % | w/v |
| Flavor | 0.1 % | v/v |
| Water QS. | 5 cc. | |

EXAMPLE 12

A proper size batch of suppositories are prepared so that each suppository will contain:

| Table 3, compound h. | 10 mg. |
|---|---|
| Wecobbe M ® | 2.5 grams |

EXAMPLE 13

Parenteral composition suitable for intramuscular administration is prepared so that each ml. contains:

| Compound of Example 6 | 10 mg. |
|---|---|

| | | |
|---|---|---|
| Polysorbate 80 | 1 mg. | |
| Benzyl Alcohol | 1.5% | v/v |
| Sodium Chloride - add enough quantity to make isotonic solution | | |
| Water for Injection QS. | 1 ml. | |

A wide variety of other pharmaceutical carriers, diluents, and additives can be used. These are described in "Remmington's Pharmaceutical Sciences" by E. W. Martin, a well-known reference in this field.

I claim:

1. A compound of the formula:

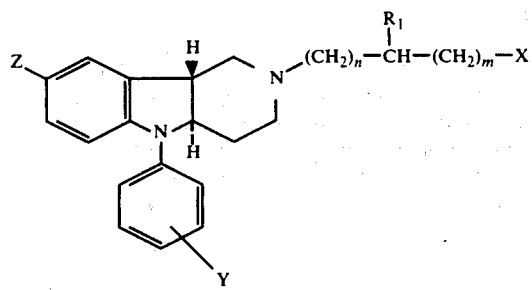

wherein
Z = H, F, Cl, or Br;
Y = H, F, Cl, Br, or OCH$_3$;

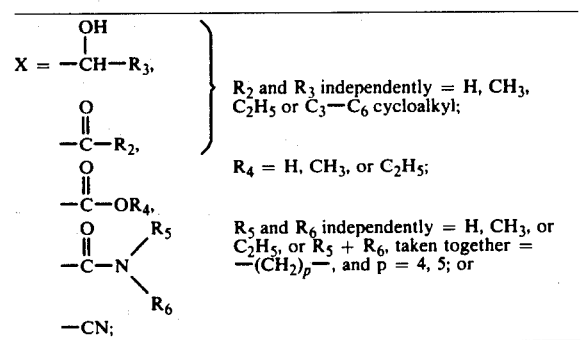

$R_2$ and $R_3$ independently = H, CH$_3$, C$_2$H$_5$ or C$_3$—C$_6$ cycloalkyl;

$R_4$ = H, CH$_3$, or C$_2$H$_5$;

$R_5$ and $R_6$ independently = H, CH$_3$, or C$_2$H$_5$, or $R_5$ + $R_6$, taken together = —(CH$_2$)$_p$—, and p = 4, 5; or $R_1$ = H, CH$_3$, or C$_2$H$_5$;
and
m and n, independently, = 0–4;
provided that than when m + n = 0, $R_1 \neq$ C$_2$H$_5$, and acid addition salts thereof with pharmaceutically suitable acids.

2. A compound of claim 1 in which m + n = 0–4.

3. A compound of claim 2 wherein

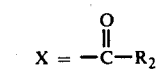

m + n = 0-2

$R_1$ = H $R_2$ = CH$_3$.

4. A compound of claim 2 wherein

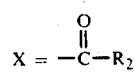

m + n = 1

$R_1$ = H $R_2$ = C$_2$H$_5$ or C$_3$—C$_6$ cycloalkyl.

5. A compound of claim 2 wherein

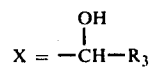

m + n = 0-2

$R_1$ = H $R_3$ = CH$_3$.

6. A compound of claim 2 wherein

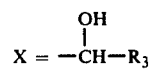

m + n = 1

$R_1$ = H $R_3$ = C$_2$H$_5$ or C$_3$—C$_6$ cycloalkyl.

7. A compound of claim 2 wherein

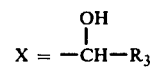

$R_1$ = H $R_3$ = H.

8. A compound of claim 2 wherein

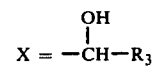

m + n = 1

$R_1$ = CH$_3$ $R_3$ = H.

9. A compound of claim 2 wherein
X = —C≡N
$R_1$ = H.

10. A compound of claim 2 wherein
X = —C≡N
m + n = 1
$R_1$ = CH$_3$.

11. A compound of claim 2 wherein

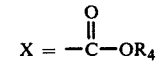

$R_1$ = H $R_4$ = H, CH$_3$ or C$_2$H$_5$.

12. A compound of claim 2 wherein

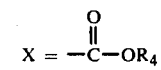

m + n = 1

$R_1$ = CH$_3$

-continued
R₄ = H, CH₃ or C₂H₅.

13. A compound of claim 2 wherein

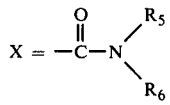

m + n = 2

R₁ = H

R₅ = —C₂H₅

R₆ = —C₂H₅.

14. A compound of claim 2 wherein

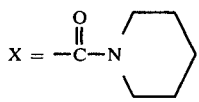

m + n = 2-3

R₁ = H.

15. The compound of claim 2 which is (+)-trans-1,3,4,4a,5,9b-hexahydro-5-phenyl-2H-pyrido[4,3-b]indole-2-butyric acid, hydrochloride salt.

16. The compound of claim 2 which is (±)-trans-1,3,4,4a,5,9b-hexahydro-5-phenyl-2H-pyrido[4,3-b]indole-2-butyric acid, hydrochloride salt.

17. The compound of claim 2 which is (±)-trans-1,3,4,4a,5,9b-hexahydro-5-phenyl-2H-pyrido[4,3-b]indole-2-butyric acid, ethyl ester, hydrochloride salt.

18. The compound of claim 2 which is (±)-trans-1,3,4,4a,5,9b-hexahydro-5-phenyl-2H-pyrido[4,3-b]indole-2-hexanoic acid, ethyl ester, hydrochloride salt.

19. A tranquilizing composition comprising a pharmaceutically suitable carrier and an effective tranquilizing amount of a compound of claim 2.

20. A tranquilizing composition comprising a pharmaceutically suitable carrier and an effective tranquilizing amount of a compound of claim 3.

21. A tranquilizing composition comprising a pharmaceutically suitable carrier and an effective tranquilizing amount of a compound of claim 4.

22. A tranquilizing composition comprising a pharmaceutically suitable carrier and an effective tranquilizing amount of a compound of claim 5.

23. A tranquilizing composition comprising a pharmaceutically suitable carrier and an effective tranquilizing amount of a compound of claim 6.

24. A tranquilizing composition comprising a pharmaceutically suitable carrier and an effective tranquilizing amount of a compound of claim 7.

25. A tranquilizing composition comprising a pharmaceutically suitable carrier and an effective tranquilizing amount of a compound of claim 8.

26. A tranquilizing composition comprising a pharmaceutically suitable carrier and an effective tranquilizing amount of a compound of claim 9.

27. A tranquilizing composition comprising a pharmaceutically suitable carrier and an effective tranquilizing amount of a compound of claim 10.

28. A tranquilizing composition comprising a pharmaceutically suitable carrier and an effective tranquilizing amount of a compound of claim 11.

29. A tranquilizing composition comprising a pharmaceutically suitable carrier and an effective tranquilizing amount of a compound of claim 12.

30. A tranquilizing composition comprising a pharmaceutically suitable carrier and an effective tranquilizing amount of a compound of claim 13.

31. A tranquilizing composition comprising a pharmaceutically suitable carrier and an effective tranquilizing amount of a compound of claim 14.

32. A tranquilizing composition comprising a pharmaceutically suitable carrier and an effective tranquilizing amount of a compound of claim 15.

33. A tranquilizing composition comprising a pharmaceutically suitable carrier and an effective tranquilizing amount of a compound of claim 16.

34. A tranquilizing composition comprising a pharmaceutically suitable carrier and an effective tranquilizing amount of a compound of claim 17.

35. A tranquilizing composition comprising a pharmaceutically suitable carrier and an effective tranquilizing amount of a compound of claim 18.

36. A method for producing a tranquilizing effect in warm-blooded animals comprising administering to said warm-blooded animals an effective tranquilizing amount of a compound of claim 2.

37. A method for producing a tranquilizing effect in warm-blooded animals comprising administering to said warm-blooded animals an effective tranquilizing amount of a compound of claim 3.

38. A method for producing a tranquilizing effect in warm-blooded animals comprising administering to said warm-blooded animals an effective tranquilizing amount of a compound of claim 4.

39. A method for producing a tranquilizing effect in warm-blooded animals comprising administering to said warm-blooded animals an effective tranquilizing amount of a compound of claim 5.

40. A method for producing a tranquilizing effect in warm-blooded animals comprising administering to said warm-blooded animals an effective tranquilizing amount of a compound of claim 6.

41. A method for producing a tranquilizing effect in warm-blooded animals comprising administering to said warm-blooded animals an effective tranquilizing amount of a compound of claim 7.

42. A method for producing a tranquilizing effect in warm-blooded animals comprising administering to said warm-blooded animals an effective tranquilizing amount of a compound of claim 8.

43. A method for producing a tranquilizing effect in warm-blooded animals comprising administering to said warm-blooded animals an effective tranquilizing amount of a compound of claim 9.

44. A method for producing a tranquilizing effect in warm-blooded animals comprising administering to said warm-blooded animals an effective tranquilizing amount of a compound of claim 10.

45. A method for producing a tranquilizing effect in warm-blooded animals comprising administering to said warm-blooded animals an effective tranquilizing amount of a compound of claim 11.

46. A method for producing a tranquilizing effect in warm-blooded animals comprising administering to said warm-blooded animals an effective tranquilizing amount of a compound of claim 12.

47. A method for producing a tranquilizing effect in warm-blooded animals comprising administering to said warm-blooded animals an effective tranquilizing amount of a compound of claim 13.

48. A method for producing a tranquilizing effect in warm-blooded animals comprising administering to said warm-blooded animals an effective tranquilizing amount of a compound of claim 14.

49. A method for producing a tranquilizing effect in warm-blooded animals comprising administering to said warm-blooded animals an effective tranquilizing amount of the compound of claim 15.

50. A method for producing a tranquilizing effect in warm-blooded animals comprising administering to said warm-blooded animals an effective tranquilizing amount of the compound of claim 16.

51. A method for producing a tranquilizing effect in warm-blooded animals comprising administering to said warm-blooded animals an effective tranquilizing amount of the compound of claim 17.

52. A method for producing a tranquilizing effect in warm-blooded animals comprising administering to said warm-blooded animals an effective tranquilizing amount of the compound of claim 18.

* * * * *